(12) United States Patent
Nouvel et al.

(10) Patent No.: US 8,481,020 B2
(45) Date of Patent: Jul. 9, 2013

(54) PHEROMONE COMPOSITIONS AND METHODS OF USE

(75) Inventors: Larry Nouvel, Plano, TX (US); Luis Rios, Pembroke Pines, FL (US); Cuong Tu Ba, Miami, FL (US)

(73) Assignee: Sergeant's Pet Care Products, Inc., Omaha, NE (US)

( * ) Notice: Subject to any disclaimer, the term of this patent is extended or adjusted under 35 U.S.C. 154(b) by 0 days.

(21) Appl. No.: 12/974,565

(22) Filed: Dec. 21, 2010

(65) Prior Publication Data

US 2011/0150822 A1      Jun. 23, 2011

Related U.S. Application Data

(60) Provisional application No. 61/288,643, filed on Dec. 21, 2009.

(51) Int. Cl.
*A01N 25/02* (2006.01)

(52) U.S. Cl.
USPC ............. 424/84; 424/405; 424/406; 514/560; 514/724; 514/760

(58) Field of Classification Search
None
See application file for complete search history.

(56) References Cited

U.S. PATENT DOCUMENTS

| | | | |
|---|---|---|---|
| 6,077,867 A | 6/2000 | Pageat | |
| 6,169,113 B1 | 1/2001 | Pageat | |
| 6,384,252 B1 * | 5/2002 | Pageat | ........................... 554/223 |
| 2009/0275670 A1 * | 11/2009 | Marshall | .................... 514/772.3 |

OTHER PUBLICATIONS

International Search Report and Opinion issued in PCT/US10/61564 dated Mar. 3, 2011.

* cited by examiner

*Primary Examiner* — Neil Levy
(74) *Attorney, Agent, or Firm* — Polsinelli PC

(57) ABSTRACT

Pheromone compositions based on a combination of squalene, linoleic acid and 1-docosanol are described. The compositions are useful for behavior modification in mammals that exhibit undesirable or harmful stress-related behaviors.

8 Claims, 2 Drawing Sheets

PHEROMONE COMPOSITIONS AND METHODS OF USE

CROSS REFERENCE TO RELATED APPLICATION

This application claims the benefit of U.S. Provisional Application Ser. No. 61/288,643 filed on Dec. 21, 2009, the disclosure of which is hereby incorporated by reference in its entirety.

THE NAMES OF THE PARTIES TO A JOINT RESEARCH AGREEMENT

The presently claimed invention was made by or on behalf of the below listed parties to a joint research agreement. The joint research agreement was in effect on or before the date the claimed invention was made and the claimed invention was made as a result of the activities undertaken within the scope of the joint research agreement. The parties to the joint research agreement are Sergeant's Pet Care Products, Inc. and Gerald Marshall.

FIELD OF THE INVENTION

This invention relates generally to the field of animal behavior and more particularly to pheromone compositions and methods of use for modifying animal behavior.

BACKGROUND

A pheromone is a chemical signaling compound naturally produced by many animals that elicits a predictable and specific behavioral response in another member of the same species. Pheromone compounds and functions vary and are thought to include alarm pheromones, food trail pheromones, reproductive pheromones, and probably many others affecting animal behavior. Although originally and most well documented in insect species, pheromones are the subject of increasing study and recognition is growing of the role that pheromones play in modifying the behavior of mammalian species.

In mammals pheromones are thought to be detected by olfactory membranes or by the vomeronasal organ (VNO or Jacobson's organ), which is positioned between the nose and mouth and functions as the first stage of the accessory olfactory system. However, unlike regular olfactory membranes, the VMO is connected directly to the mid-brain and thus enjoys the shortest organ-to-brain distance in mammals. This feature allows pheromones present in extremely small quantities to very selectively trigger certain biochemical processes in the animal. Moreover, pheromone signals go directly to subconscious areas of brain without being processed by the conscious brain, and thus pheromone effects are both rapid and subconscious. While the precise mechanisms underlying pheromone effects on the mammalian brain remain to be further explored and characterized, a growing body of evidence indicates clear behavioral effects likely involving at least hormonal responses. For example, studies of the house mouse have revealed a complex pheromone communication system for signaling inter-male aggression and dominance, mating readiness, and for signaling stress to the other members of the colony. All of these behaviors have demonstrated correlations with hormonal pathways. Pheromone effects may also be mediated by basic olfactory mechanisms and behavioral effects associated with olfactory processing. For example, olfactory processing is known to be important for newborn mammals. Newborns, including humans, can identify the mother from her scent. This process may be crucial to bonding and survival and is thought a likely candidate for involving pheromone mechanisms in mammals. Thus growing evidence is consistent with an important role for pheromones in controlling mammalian behavior, and particularly those behaviors associated with bonding, socialization, aggression and stress.

In domestic, farm, and zoo animals, including dogs, cats, horses, swine, cattle, tigers, lions, bears, elephants, etc., fear and anxiety arising from various sources frequently result in harmful or annoying behaviors that are not well tolerated by the affected animal, other animals or human owners/handlers. For example, separation anxiety in dogs frequently results in soiling, excessive chewing or licking, property destruction, constant barking, and hyperactivity. Pet cats under stress, for instance, from the introduction of a new cat to the household, will often spray, scratch, claw, and make other displays of aggression. Generally, a need is recognized for compositions and methods that can be used on any affected domestic, farm, or zoo animal to control such undesirable behaviors.

SUMMARY OF THE INVENTION

The inventors have discovered novel pheromone compositions that are useful for modifying behavior in mammals, and are particularly useful for modifying objectionable behaviors in domestic animals that result from stress or anxiety. The compositions are based in part on the surprising finding that squalene-based compositions (i.e. compositions comprising at least 30% by weight of squalene) are effective at modifying stress- or anxiety-related behaviors in domestic animals.

Accordingly, in one aspect there is provided a pheromone composition for modifying behavior of a mammal, the composition comprising a mixture of at least 30% (% w/w) squalene, at least 10% (% w/w) linoleic acid, and at least 1% (% w/w) 1-docosanol.

In another aspect there is provided a pheromone composition for modifying behavior of a mammal, the composition comprising 30%-80% (% w/w) squalene, 10-75% (% w/w) linoleic acid, and 1%-10% (% w/w) 1-docosanol.

In another aspect there is provided a pheromone solution for modifying behavior of a mammal, the composition comprising about 1%-15% by volume of a mixture of 30%-35% (% w/w) squalene, 55-65% (% w/w) linoleic acid, 2%-5% (% w/w) 1-docosanol, and 1%-5% (% w/w) cholesterol, and about 70%-90% by volume of an organic solvent.

In another aspect there is provided a pheromone solution for modifying behavior of a mammal, the composition comprising about 1%-15% by volume of a mixture of 30%-35% (% w/w) squalene, 55-65% (% w/w) linoleic acid, 2%-5% (% w/w) 1-docosanol, and 2%-10% (% w/w) of a mixture of at least two fatty acids other than linoleic acid, and about 70%-90% by volume of an organic solvent.

In another aspect there is provided a pheromone solution for modifying behavior of a mammal, the composition comprising about 1%-15% by volume of a mixture of 30%-35% (% w/w) squalene, 55-65% (% w/w) linoleic acid, 2%-5% (% w/w) 1-docosanol, 1%-5% (% w/w) cholesterol and 2%-10% (% w/w) of a mixture of at least two fatty acids other than linoleic acid, and about 70%-90% by volume of an organic solvent.

In another aspect there is provided a pheromone solution for modifying behavior of a mammal, the composition comprising about 1%-15% by volume of a mixture of 65%-70% (% w/w) squalene, 18%-21% (% w/w) linoleic acid, 2%-5% (% w/w) 1-docosanol, and 7%-9% (% w/w) of a mixture of at least two fatty acids other than linoleic acid, and about 70%-90% by volume of an organic solvent.

In another aspect there is provided a pheromone solution for modifying behavior of a mammal, the composition comprising about 1%-15% by volume of a mixture of 65%-70% (% w/w) squalene, 18%-21% (% w/w) linoleic acid, 2%-5% (% w/w) 1-docosanol, 7%-9% (% w/w) of a mixture of at least two fatty acids other than linoleic acid and 1% (% w/w) cholesterol, and about 70%-90% by volume of an organic solvent.

In a further aspect there is provided a method of modifying stress-related behavior in a mammal, the composition comprising administering to the mammal a therapeutically effective amount of a squalene-based pheromone composition, the composition comprising at least 30% (% w/w) squalene, at least 10% (% w/w) linoleic acid, and at least 1% (% w/w) 1-docosanol.

In an additional aspect there is provided a composition for modifying behavior of a mammal, the composition comprising a solid matrix into which is incorporated 10%-20% by weight of a pheromone composition, the pheromone composition comprising 30%-80% (% w/w) squalene, 10-75% (% w/w) linoleic acid, and 1%-10% (% w/w) 1-docosanol.

DETAILED DESCRIPTION OF THE INVENTION

Figure 1:
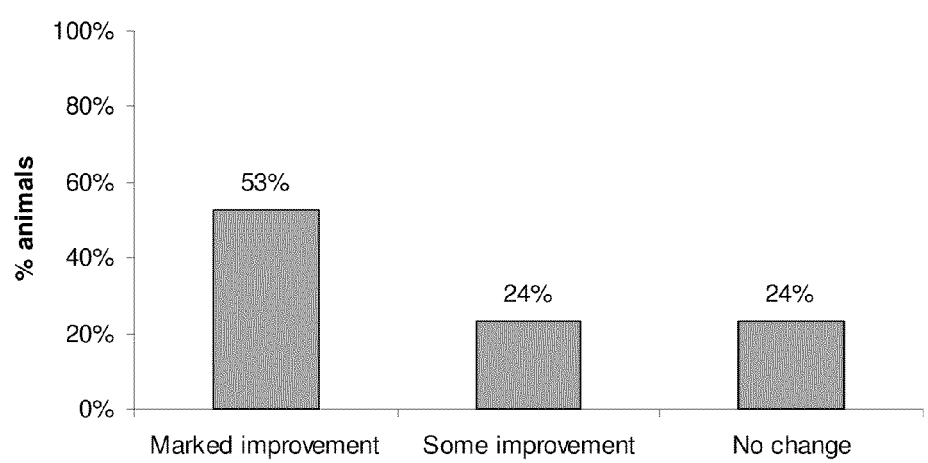
FIG. 1 is a bar graph illustrating the behavioral results obtained in a study of the effects on behavior of an exemplary pheromone composition on dogs exhibiting behavior problems.

The pheromone compositions provided herein are believed to mimic certain naturally occurring pheromones that have a calming effect on mammals. As such, the compositions are useful for controlling behavior in mammals and are especially useful for controlling stress- or anxiety-induced behavior in pets and domestic animals such as, but not limited to, dogs, cats, and horses. In particular, the pheromone compositions disclosed herein are based in part on the unexpected finding that compositions made primarily from squalene, a naturally occurring organic compound obtained from shark liver oil, and certain volatile organic compounds including certain fatty acids, demonstrate calming effects on mammals. Accordingly, the term "squalene-based" as used herein to describe the pheromone compositions refers to a composition that includes at least 30% by weight of squalene. Most surprisingly, such compositions were found to produce strong calmative effects in mammals without additionally including either palmitic acid or oleic acid, two fatty acids that are critical components in previously described pheromone compositions, such as in U.S. Pat. No. 6,077,867.

A basic pheromone composition includes at least 30% (% w/w) squalene, at least 10% (% w/w) linoleic acid, and at least 1% (% w/w) 1-docosanol (behenyl alcohol or docosyl alcohol). Preferably the composition includes 30%-80% (% w/w) squalene in combination with 10%-75% (% w/w) linoleic acid, and 1%-10% (% w/w) 1-docosanol, with the balance of the composition being made up of cholesterol or a mixture of additional fatty acids (in addition to the linoleic acid) or both cholesterol and a mixture of additional fatty acids (in addition to the linoleic acid). The mixture of additional fatty acids excludes both palmitic acid and oleic acid. Cholesterol, when included, contributes 0.1%-10% (% w/w) to the composition, and preferably contributes 1%-5% (% w/w) to the composition. Similarly, a mixture of fatty acids, when included, contributes 0.1%-10% (% w/w) to the composition, and preferably contributes 2%-9% (% w/w). When both cholesterol and a mixture of additional fatty acids are included in the composition, the combined components together contribute no more than about 10% (% w/w) to the composition.

Squalene is a natural organic compound originally obtained for commercial purposes primarily from shark liver oil, but is also derived from botanical sources, including amaranth seed, rice bran, wheat germ, and olives. As derived from shark liver oil, squalene is readily available from many commercial sources. As discussed herein, squalene comprises at least about 30% (% w/w), 35% (% w/w), 40% (% w/w), 45% (% w/w), 50% (% w/w), 55% (% w/w), 60% (% w/w), 65% (% w/w), 70% (% w/w), 75% (% w/w), 80% (% w/w), or 85% (% w/w) of the formulation. For example, the amount of squalene present in the formulation may range from about 30%-80% (% w/w) and preferably ranges from about 65%-70% (% w/w). In a further embodiment, the amount of squalene present in the formulation may range from about 30%-35% (% w/w). In a further embodiment, the amount of squalene may range from about 35%-60% (% w/w). In still another embodiment, the amount of squalene may range from about 45%-70% (% w/w).

Linoleic acid is an omega-6-fatty acid, used in the biosynthesis of arachidonic acid (AA) and some prostaglandins. It is found in the lipids of cell membranes. It is abundant in many vegetable oils, especially safflower and sunflower oils. Similarly, linoleic acid is also available from a variety of commercial sources. As discussed herein, linoleic acid comprises at least about 10% (% w/w), 15% (% w/w), 16% (% w/w), 17% (% w/w), 18% (% w/w), 19% (% w/w), 20% (% w/w), 21% (% w/w), 22% (% w/w), 23% (% w/w), 24% (% w/w), 25% (% w/w), 30% (% w/w), 35% (% w/w), 40% (% w/w), 45% (% w/w), 50% (% w/w), 55% (% w/w), 56% (% w/w), 57% (% w/w), 58% (% w/w), 59% (% w/w), 60% (% w/w), 61% (% w/w), 62% (% w/w), 63% (% w/w), 64% (% w/w), 65% (% w/w), 70% (% w/w), 75% (% w/w), or 80% (% w/w) of the formulation. For example, the amount of linoleic acid present in the formulation may range from about 10%-75% (% w/w) and preferably ranges from about 15%-25% (% w/w). In a further embodiment, the amount of linoleic acid present in the formulation may range from about 55%-65% (% w/w). In yet another embodiment, the amount of linoleic acid may range from about 18%-21% (% w/w).

1-docosanol (also known as n-docosanol, docosyl alcohol, behenic alcohol behenyl alcohol, Cachalot BE-22, Dehydag wax 22 (lanette), Emery 3304, and Loxiol VPG 1451) is a carboxylic acid generally known for antiviral therapeutic properties, and its use in the treatment of cold sores. Like squalene and linoleic acid, 1-docosanol is available from a variety of commercial sources. As discussed herein, 1-docosanol comprises at least about 1% (% w/w), 2% (% w/w), 3% (% w/w), 4% (% w/w), 5% (% w/w), 6% (% w/w), 7% (% w/w), 8% (% w/w), 9% (% w/w), or 10% (% w/w) of the formulation. For example, the amount of 1-docosanol present in the formulation may range from about 1%-10% (% w/w) and preferably ranges from about 2%-5% (% w/w). In a further embodiment, the amount of 1-docosanol present in the formulation may range from about 1%-7% (% w/w).

The cholesterol component of the current invention is generally defined as steroid found in the cell membranes and transported in the blood plasma of most animals. Cholesterol is an important precursor molecule for the biosynthesis of bile acids, steroid hormones, and several other fat-soluble vitamins. One skilled in the art will appreciate that the cholesterol component of the current invention is available from a variety of commercial sources. As discussed herein, cholesterol comprises at least about 0.1% (% w/w), 0.2% (% w/w), 0.3% (% w/w), 0.4% (% w/w), 0.5% (% w/w), 1% (% w/w), 2% (% w/w), 3% (% w/w), 4% (% w/w), 5% (% w/w), 6% (% w/w), 7% (% w/w), 8% (% w/w), 9% (% w/w), or 10% (% w/w) of the formulation. For example, the amount of cholesterol present in the formulation may range from about 0.1%-10% (% w/w) and preferably ranges from about 1%-5% (% w/w).

Any additional fatty acid included in the pheromone composition (besides linoleic acid) can be used in its pure form, i.e., as a free fatty acid or in a derivative form such as an ester, salt, alcohol, ketone, ether or amide. Fatty acids are commercially readily available from various chemical companies, typically in solid form. As discussed herein, additional fatty acids (other than linoleic acid) comprise at least about 0.1% (% w/w), 0.2% (% w/w), 0.3% (% w/w), 0.4% (% w/w), 0.5% (% w/w), 1% (% w/w), 2% (% w/w), 3% (% w/w), 4% (% w/w), 5% (% w/w), 6% (% w/w), 7% (% w/w), 8% (% w/w), 9% (% w/w), or 10% (% w/w) of the formulation. For example, the amount of additional fatty acids present in the formulation may range from about 0.1%-10% (% w/w) and preferably ranges from about 6%-9% (% w/w). In a further embodiment the amount of additional fatty acids present in the formulation may range from about 2%-10% (% w/w).

To dissolve a fatty acid obtained in solid form, the fatty acid is typically added to a solvent under constant agitation and at an elevated temperature of about 37° C. to about 38° C. A fatty acid can also be microencapsulated and suspended in water to form a water suspension. Fatty acids suitable for inclusion in the composition include propanoic acids such as propionic acid, butanoic acids such as butyric acid, pentanoic acids such as valeric acid, hexanoic acid such as caproic acid, heptanoic acids such as enanthic acid, octanoic acids such as caprylic acid, nonanoic acids such as pelargonic acid, decanoic acids such as capric acid, undecanoic acids such as undecylic acid, dodecanoic acids such as lauric acid, tridecanoic acids such as tridecylic acid, heptadecanoic acids such as margaric acid, octadecanoic acids such as stearic acid, eicosanoic acids such as arachidic acid, heneicosanoic acids such as heneicosylic acid, tricosanoic acids such as tricosylic acid, tetracosanoic acids such as lignoceric aid, pentacosanoic acids such as pentacosylic acid, hexacosanoic acids such as cerotic acid, heptacosanoic acids such as heptaosylic acid, octacosanoic acids such as montanic acid, nonacosanoic acids such as nonacosylic acid, triacontanoic acids such as melissic acid, henatriacontanoic acids such as henatriacontylic acid, dotriacontanoic acids such as lacceroic acid, tritriacontanoic acids such as psyllic acid, tetratriacontanoic acids such as geddic acid, pentatriacontanoic acids such as ceroplastic acid, hexatriacontanoic acids such as hexatriacontylic acid, nonanedioic acids such as azelaic acid, tetradecanoic acids such as myristic acid, pentadecyclic acids such as n-pentadecanoic acid, and heptanedioic acids such as pimelic acid. Derivatives of these fatty acids such as esters or salts can also be used in the composition.

It is preferred that if additional fatty acids are included in the pheromone composition (other than linoleic acid), a mixture of at least two additional fatty acids are used. In one preferred embodiment of the current invention, the pheromone composition incorporates a mixture of fatty acids (other than linoleic acid) comprising approximately 1%-1.6% (% w/w) myristic acid, 4.5%-6% (% w/w) n-pentadecanoic acid, and 0.1%-0.3% (% w/w) lauric acid. In another preferred embodiment of the current invention, the pheromone composition incorporates a mixture of fatty acids (other than linoleic acid) comprising approximately 1%-1.6% (% w/w) myristic acid, 4.5%-6% (% w/w) n-pentadecanoic acid, 0.1%-0.3% (% w/w) lauric acid, 0.8%-3% (% w/w) azelaic acid, and 0.8%-3% (% w/w) pimelic acid. In yet another preferred embodiment of the current invention, the pheromone composition incorporates a mixture of fatty acids (other than linoleic acid) comprising approximately 1%-1.6% (% w/w) myristic acid, 0.5%-1.6% (% w/w) n-pentadecanoic acid, 0.1%-0.3% (% w/w) lauric acid, 4%-6% (% w/w) capric acid, 0.8%-3% (% w/w) azelaic acid, and 0.8%-3% (% w/w) pimelic acid. In an additional preferred embodiment of the current invention, the pheromone composition incorporates a mixture of fatty acids (other than linoleic acid) comprising approximately 1%-1.6% (% w/w) myristic acid, 0.5%-1.6% (% w/w) n-pentadecanoic acid, and 0.1%-0.3% (% w/w) lauric acid.

Other compounds optionally included in the pheromone composition are amines, glycol, glycerol, and non-toxic lipophilic anti-oxidants such as butylated hydroxytoluene ("BHT", also known as butylhydroxytoluene). In a preferred embodiment of the current invention, the pheromone composition comprises approximately 0.001%-1% (% w/w) butylated hydroxytoluene. The basic pheromone composition can be further combined with any carrier material that preserves the bioactivity of the squalene, linoleic acid and additional fatty acids, if included. Such carrier materials include, but are not limited to resins, liposomes, vesicles, carrier proteins and the like.

The pheromone composition is typically used by administering to the subject animal a therapeutically effective amount of the pheromone composition through any method allowing delivery of the composition by inhalation by the animal. Such methods of administration include, for example, simply placing or distributing the composition in the environment of the animal, either by incorporating the composition into a wearable device such as a collar, or by applying (e.g. spraying) the composition to surfaces in the living environment of the animal. The term "therapeutically effective" describes an amount of the pheromone compound that is sufficient to produce a noticeable modification, i.e. improvement, of animal behavior in the subject animal, as determined according to behavioral observations as described herein.

For example, a pheromone composition in liquid or solid form can be incorporated in various ways as are generally well known into a solid carrier material to form a collar or tag, and the collar or tag is then worn by the mammal. The solid carrier material is selected from among those materials, typically polymeric compounds, generally recognized to be suitable for release of active compounds (e.g. pesticidal compounds) and set forth in further detail herein below. Alternatively, the pheromone composition is combined with a solvent to form a liquid pheromone solution and the liquid pheromone solution be further prepared in various formulations suitable for delivery to the mammal by inhalation. For example, liquid solutions can be further prepared according to methods well known in the art as a spray, gel, foam, shampoo, or spot-on formulation.

In an exemplary embodiment the pheromone composition is incorporated into a solid carrier material to form a matrix containing the pheromone composition. The solid carrier material containing the pheromone composition is then formed into a collar as is well known and amply described in the art, for example in U.S. Pat. No. 3,852,416. Typically an admixture of an active (e.g. the pheromone composition) and a carrier material providing the matrix is formed into strips through an extrusion process, and each strip is then formed a collar by including a fastening device such as a buckle, snap or hook. The solid carrier material forming the matrix into which the pheromone composition is incorporated is for example a polymer or polymer mixture with suitable release characteristics such that the pheromone composition is released from the collar to be inhaled by the animal. The pheromone composition contributes 0.1%-50% (% w/w), preferably 5%-30% (% w/w), and more preferably 10%-200% (% w/w) by weight of the collar.

Suitable polymers for forming a solid substrate for making collar are well known and include, but are not limited to, polyethylene, polyvinyl acetate, ethylene acid copolymers, ethylene acrylates, polyurethanes, styrene-butadiene, polyvinyl butyral, polyvinyl chloride (PVC), polyolefin, polyacrylate, and polymethacrylate esters, and silicon polymer. The polymers can contribute 0.1-99% by weight of the collar, and typically will contribute 90%-95% by weight of the collar. Plasticizers can be incorporated into the mixture to render the polymer resin more flexible. Suitable such plasticizers include phosphoric acid esters (e.g. tricresyl phosphate) or phthalic acid esters (such as dioctyl phthalate). The collar may also include other additives such as stabilizers, for example antioxidants to protect the collar material from degradation by UV light and other oxidizing factors. Lubricants, colorants, and fillers may also be included.

The pheromone composition is generally solid in nature, but it can also be dissolved or diluted in a nonaqueous organic solvent or solvent mixture to form a pheromone solution. Suitable solvents are generally known within the art and are recognized to include lipophilic organic diluents, alcohols, ethylene glycol, propylene glycol, dipropylene glycol, ether, chloroform, benzene, carbon disulfide, oils including non-volatile and volatile oils, and combinations thereof. In an exemplary embodiment, the pheromone composition is combined with an organic solvent or solvents and diluents to form a pheromone solution in one of various liquid or liquid-based forms such as sprays, aerosols, gels, dips, shampoos, spot treatments, microencapsulated products and so on. For example, the basic composition can be dissolved in a suitable alcohol and supplied in a liquid form such as a spray or for use in a plug-in diffuser. Suitable alcohols include ethanol, propanol, isopropanol, butanol, pentanol, hexanol, heptanol, octanol, and phenyl ethyl alcohol. In a preferred embodiment, the alcohols comprise ethanol, isopropanol, butanol, and phenyl ethyl alcohol. An alcohol solvent can be combined with a lipophilic organic diluent or carrier such as ethylene glycol, propylene glycol, dipropylene glycol, dipropylene glycol monoethyl ether, dipropylene glycol methyl ether, or Dow Corning® Q7-9180 silicone liquid. In a preferred embodiment, the solvent is a combination of dipropylene glycol and an alcohol selected from the group consisting of ethanol, isopropanol, and butanol. In an exemplary embodiment, the solvent comprises a combination of dipropylene glycol and isopropanol. The basic pheromone composition is diluted to form a solution wherein the composition contributes about 0.5%-57% by volume, preferably 1%-40% by volume, more preferably 1%-30% by volume, and even more preferably 1%-15% by volume of the solution, in a mixture of an alcohol and dipropylene glycol, wherein the alcohol contributes about 70%-90% by volume and the dipropylene glycol contributes about 5%-10% by volume to the solution.

The concentration of the aforementioned components including squalene, linoleic acid, cholesterol and other fatty acid mixture included in the basic pheromone composition, may vary within the aforementioned ranges, depending upon the intended final form and use. However, it will be recognized that concentrations of the components that can be used are readily ascertainable and can be assayed according to the behavioral methods set forth herein.

Thus, in one embodiment, the composition comprises 30%-80% (% w/w) squalene, 10%-75% (% w/w) linoleic acid, 1%-10% (% w/w) 1-docosanol, and 0.1%-10% (% w/w) of a mixture of at least two fatty acids other than linoleic acid. In another embodiment, the basic composition includes 30%-80% (% w/w) squalene, 10%-75% (% w/w) linoleic acid, 1%-10% (% w/w) 1-docosanol, and 0.1%-10% (% w/w) cholesterol. In an additional embodiment, the basic composition includes 30%-80% (% w/w) squalene, 10%-75% (% w/w) linoleic acid, 1%-10% (% w/w) 1-docosanol, and 0.1%-10% (% w/w) of a mixture of cholesterol and at least two fatty acids other than linoleic acid. The composition optionally further includes a small amount of a lipophilic antioxidant such as BHT, at least about 0.005% (% w/w), no more than about 0.1% (% w/w), and most typically about 0.01% (% w/w).

In another embodiment, the composition comprises 65%-75% (% w/w) squalene, 18%-21% (% w/w) linoleic acid, 2%-5% (% w/w) 1-docosanol, and 0.1%-10% (% w/w) of a mixture of cholesterol and at least two fatty acids other than linoleic acid.

In another embodiment, the composition comprises 30%-35% (% w/w) squalene, 55%-65% (% w/w) linoleic acid, 2%-5% (% w/w) 1-docosanol, and 0.1%-10% (% w/w) of a mixture of cholesterol and at least two fatty acids other than linoleic acid.

In another embodiment, the composition comprises 30%-80% (% w/w) squalene, 10%-75% (% w/w) linoleic acid, 1%-10% (% w/w) 1-docosanol, and 0.1%-10% (% w/w) of a mixture of at least two fatty acids other than linoleic acid, wherein the composition is in solution wherein the composition contributes about 1%-15% by volume of the solution in a mixture of an alcohol and dipropylene glycol, wherein the alcohol contributes about 70%-90% by volume and the dipropylene glycol contributes about 5%-10% by volume to the solution.

In another embodiment, the composition comprises 30%-80% (% w/w) squalene, 10%-75% (% w/w) linoleic acid, 1%-10% (% w/w) 1-docosanol, and 0.1%-10% (% w/w) cholesterol, and the composition is in solution wherein the composition contributes about 1%-15% by volume of the solution in a mixture of an alcohol and dipropylene glycol, wherein the alcohol contributes about 70%-90% by volume and the dipropylene glycol contributes about 5%-10% by volume to the solution.

In one exemplary embodiment the composition includes 30%-35% (% w/w) squalene, 55-65% (% w/w) linoleic acid, 2%-5% (% w/w) 1-docosanol, and 1%-5% (% w/w) cholesterol.

In another exemplary embodiment the composition includes 30%-35% (% w/w) squalene, 55%-65% (% w/w) linoleic acid, 2%-5% (% w/w) 1-docosanol, and 2%-10% (% w/w) of a mixture of at least two fatty acids other than linoleic acid.

In another exemplary embodiment the composition includes 30%-35% (% w/w) squalene, 55%-65% (% w/w) linoleic acid, 2%-5% (% w/w) 1-docosanol, 1%-5% (% w/w) cholesterol and 2%-10% (% w/w) of a mixture of at least two fatty acids other than linoleic acid.

In another exemplary embodiment the composition includes 65%-70% (% w/w) squalene, 18%-21% (% w/w) linoleic acid, 2%-5% (% w/w) 1-docosanol, and 6%-9% (% w/w) of a mixture of at least two fatty acids other than linoleic acid.

In another exemplary embodiment the composition includes 65%-70% (% w/w) squalene, 18%-21% (% w/w)

linoleic acid, 2%-5% (% w/w) 1-docosanol, 6%-9% (% w/w) of a mixture of at least two fatty acids other than linoleic acid and 1% (% w/w) cholesterol.

In another aspect the present disclosure encompasses a method of modifying stress-related behavior in a mammal by exposing the mammal to a therapeutically effective amount of a squalene-based pheromone composition, wherein the composition comprises at least 30% (% w/w) squalene, at least 10% (% w/w) linoleic acid, and at least 1% (% w/w) 1-docosanol. The mammal can be exposed to the composition by any method allowing inhalation by the mammal over a period of time sufficient to effect a modification of the target behavior, as determined according to behavioral observations. Typically the exposure will be over a period of at least several minutes to a few hours, but can be over a period of days or weeks as may be needed to achieve a satisfactory behavioral effect, and can be continued over a period of weeks, months or longer depending on the particular mammal and situation. For example, a mammal suffering from a temporarily induced anxiety, for example a pet anxious over a trip to a veterinary office, may require a brief exposure to the pheromone composition before, during or after the trip to relieve the anxiety and associated behavior. In contrast, a mammal exposed to a stressful stimulus for a longer and continual period, such as a pet exposed to a new pet in the household, may benefit from regular exposure to the pheromone composition.

Following preparation, the pheromone compositions and liquid pheromone solutions thereof can be readily tested for efficacy for stress-relief in mammalian species. Commonly recognized sources of stress in mammals include for example weaning, transportation especially in motorized vehicles, boredom, lack of exercise, separation anxiety, loud noises, introduction to new people or animals and visits to a veterinary office. Mammals that are stressed by exposure to such events or conditions will typically exhibit highly undesirable stress-related behavioral symptoms. Such stress behaviors are commonly recognized and include for example fearful behavior such as cowering or shaking; excessive chewing or barking; hyperactivity; aggressive behavior toward people or other animals such as growling, snappishness or biting; property destruction; and frequent urination or soiling. The efficacy of the pheromone composition can be tested for example by having subject mammals wear a collar incorporating the pheromone composition, or by applying the composition in the form of a liquid spray, liquid diffuser or the like in a physical area associated with the stress-inducing conditions for any given animal. In either case, the pheromone composition is sufficiently volatile for the mammal to inhale and thus be exposed to a sufficient amount of the pheromone composition to produce a noticeable behavioral effect. For example, a reduction in stress-related outward behaviors is readily ascertainable (e.g. noticeable reduction in aggressive displays, barking or chewing) and can be supplemented by observing other physical indicators of stress such heart rate, weight changes, and secretion of stress hormones such as cortisol.

In use, the pheromone composition can be implemented in a number of different ways depending in part on the targeted mammal(s) and behavior desired to be modified. A liquid solution containing the composition can simply be applied directly to the coat or skin of a mammal, or sprayed on surfaces or objects in the mammal's environment, or diffused or sprayed into the air in the mammal's environment. For example, an exemplary liquid spray formulation containing 1%-40% by volume of the pheromone composition (dissolved in a suitable solvent) can be sprayed, for example, on floors, walls or animal toys about once a week, or once or several times daily, as needed, to obtain the desired behavioral modification. Alternatively, for example, a liquid formulation containing 1%-15% by volume of the pheromone composition can delivered by a diffuser such as a plug-in diffuser commercially available from as Central Life Sciences/Farnam Companies Inc. (Phoenix, Ariz.) as the Comfort Zone® Diffuser (sold with Feliway® or DAP® (Dog Appeasing Pheromone)). Alternatively, the composition in liquid or solid form can be incorporated in a plasticized material such as PVC or the like that can then be formed into a tag, or in strips to form a collar.

As used herein, the word "mammal" is interchangeable with the word "animal" and encompasses any group of vertebrates the females of which have milk-secreting glands, including man. Examples of mammals include, but are not limited to, domestic mammals such as cats and dogs; small mammals, such as hamsters, rabbits, ferrets, rats, mice, and guinea pigs; commercial mammals, such as horses, sheep, cattle, and swine; and mammals in captivity, such as apes, chimpanzees, tigers, lions, bears, elephants, zebras, and the like.

As various changes could be made in the above formulations, products and methods without departing from the scope of the invention, it is intended that all matter contained in the above description and in the examples given below, shall be interpreted as illustrative and not in a limiting sense.

EXAMPLES

Example 1

Pheromone Compositions

Table 1 lists the formulations of five exemplary pheromone compositions (A, B, C, D, and E) prepared according to the present teachings. All amounts are presented as % w/w of the composition.

TABLE 1

| COMPONENT | FORMULATION (% w/w) | | | | |
| --- | --- | --- | --- | --- | --- |
|  | A | B | C | D | E |
| Linoleic Acid | 59.69 | 20 | 20 | 60 | 61.19 |
| Myristic Acid | 1.5 | 1.5 | 1 |  | 1 |
| n-Pentadecanoic acid (Pentadecylic Acid) | 4.5 | 5.5 | 1.5 |  | 0.5 |
| Cholesterol | 1 |  | 1 | 5 | 1 |
| Lauric Acid | 0.3 | 0.3 | 0.3 |  | 0.3 |
| 1-Docosanol (Behenyl alcohol or Docosyl Alcohol) | 2 | 2 | 2 | 4.99 | 2 |
| Squalene (Shark Origin) | 31 | 67.69 | 68.19 | 30 | 34 |
| Capric Acid |  |  | 4 |  |  |
| Azelaic Acid |  | 1.5 | 1 |  |  |
| BHT | 0.01 | 0.01 | 0.01 | 0.01 | 0.01 |
| Pimelic Acid (Heptanedioic acid) |  | 1.5 | 1 |  |  |
| TOTAL | 100 | 100 | 100 | 100 | 100 |

Example 2

Behavior Modification in Dogs

The primary objective of this study was to assess the efficacy of a pheromone collar comprising the formulation of the present invention in controlling stress related behaviors in dogs. The collar was formed from an extrusion process using PVC into which a composition according to formula C from Example 1 was incorporated at 6% by weight (of the collar). All of the dogs enrolled in the study were client-owned dogs presented to a veterinary practice for behavior-related problems. Owners were invited to participate in the study if the dog exhibited one or more of the following symptoms: nervousness or fear of noise; timidity/fear of other dogs or people; excessive chewing; excessive barking; aggressive displays toward other dogs or the owner; soiling when left alone; and/or hyperactivity.

The testing period lasted anywhere from one to three months. Animal subjects acted as their own controls. All animals were treated with a plasticized collar in which the composition of formula C was incorporated. Nineteen dogs were enrolled in the study. Two animals were excluded from the final data analysis, leaving data from a total of seventeen animals. The two excluded animals shared a household and each managed to detach the other's collar shortly after the collars were applied.

Behavioral characteristics of all subject dogs are set forth in Table 2 below.

TABLE 2

| Dog ID | Dog Name | Dog Type | Age | Type of Behavior Disorder |
|---|---|---|---|---|
| 1 | Neeko | Rottweiler Border Collie Cross | 9 months old | Nervous of noises, timid with other dogs and people. |
| 2 | Riddick | Rottweiler | 2 year old | Nervous of noises and hyperactive in the house. |
| 3 | Rosie | Staffie | 2½ year old | Barked at everything through the window and was hyperactive. |
| 4 | Rufus | Staffie | 2 year old | Very nervous and timid and shied away from other dogs. |
| 5 | Dixie | Staffie cross | 1 year old | Very hyperactive, over the top playful and chewed a lot. |
| 6 | Tyson | American Mastiff | 8 year old | Soiling. Very smelly dog. |
| 7 | Murphy | Cocker Spaniel | 1 year old | Very hyperactive and soiling/smelly. |
| 8 & 9 | Buster and Barney | Border Terriers | Both 2 years old | Destructive house |
| 10 | Diesel | Collie cross with Belgian Sheppard | 7 months old | Very snappy with owners, did not like to be fussed with or touched. |
| 11 | Artimakay | Deerhound | 5 months old | Constantly barking at owner for attention |
| 12 | Herby | Wirehaired Dachshund | 3 years old | Soiling/Toileting when left alone. |
| 13 | Millie | Terrier | 2 years old | Very nervous of people and big dogs. |
| 14 | Benji | Yorkshire Terrier | 1½ years old | Did not like men and was nervous of other dogs. |
| 15 | Bailey | Chocolate Labrador | 11 months old | Nervous of people he did not know and some dogs. |
| 16 | Bigun | German Sheppard cross Retriever | 9 years old | Easily stressed leading to hyperactivity |
| 17 | Mutley | Cross breed | 15 year old | Senile barking (deaf and nearly blind) |
| 18 | Piglet | Terrier cross | 4 years old | Easily stressed and suffers from polydipsia (over drinking) and polyuria (urinating excessively) |
| 19 | Dobbie | Cross breed | 9 year old | Some instances of aggressive behavior |

As illustrated in FIG. 1, 77% (or 13/17) of all animals for which data was analyzed showed a positive behavior response to the dog pheromone collar.

Example 3

Behavior Modification in Cats

A clinical field trial was conducted in 119 cats presented for one or more of the following behavior problems: urination, scratching, aggressiveness, and/or excessive timidity. Animals that presented one or more of these conditions were enrolled in the study and divided into one of two treatment groups. Animals from the first group wore a pheromone collar for a period of two months. The collar was formed from an extrusion process using PVC into which was incorporated a composition according to formula C from Example 1 at 9% by weight (of the collar). Animals from the second group were treated using a commercial plug-in cat pheromone diffuser (Comfort Zone® diffuser sold with Feliway®) for a period of two months. The study was conducted under a blind condition so that the human owners did not know the identity of the brand name, manufacturer name and composition during the course of the study. Owners were asked to answer simply "Yes" or "No" as to whether the owner noticed any behavior improvement during the course of the two month treatment period.

Figure 2:
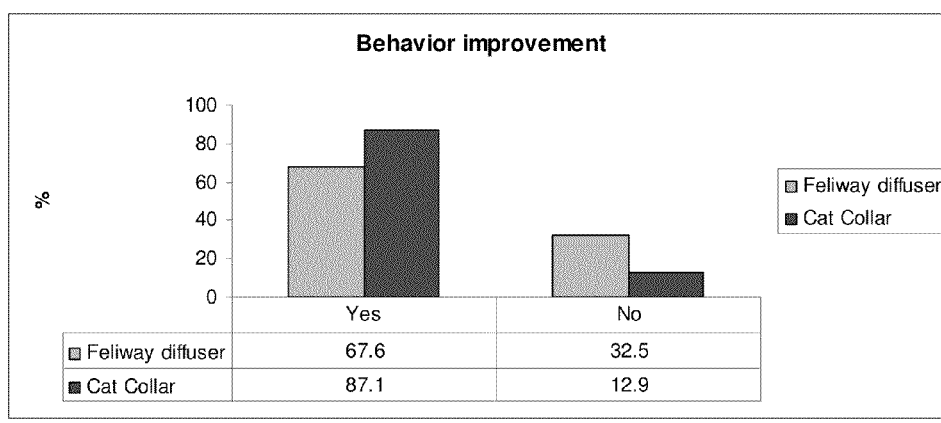
FIG. 2 is a bar graph illustrating the behavioral results obtained in a clinical field trial of a pheromone composition on cats exhibiting behavior problems.

FIG. 2 is a bar graph summarizing the results of the study and illustrating that the majority of cat owners reported noticeable behavior improvement using the composition of the present invention both in the collar and in the diffuser. Results were statistically significant at 1%.

Example 4

Liquid Compositions

Table 3 lists three liquid formulations (F, G, and H) of the pheromone composition according to the present teachings. As is shown, each liquid formulation consists of a pheromone "concentrate" composition consisting primarily of squalene and linoleic acid, plus 1-docosanol, cholesterol, additional fatty acids and BHT. The pheromone composition contributed 15.1% by volume to the final volume of each liquid formulation, after the mostly solid pheromone "concentrate" was dissolved in a mixture of dipropylene glycol and an alcohol (ethanol 190 proof (90%), isopropanol, or butanol). All amounts listed below are presented as % v/v.

TABLE 3

| | FORMULATION (% v/v) | | |
|---|---|---|---|
| COMPONENT | F | G | H |
| Dipropylene Glycol | 7.178 | 7.178 | 7.178 |
| Ethanol 190 proof (90%) | 77.600 | | |
| Isopropanol | | 77.600 | |

TABLE 3-continued

| COMPONENT | FORMULATION (% v/v) | | |
|---|---|---|---|
| | F | G | H |
| Butanol | | | 77.600 |
| Linoleic Acid | 9.362 | 9.362 | 9.362 |
| Myristic Acid | 0.151 | 0.151 | 0.151 |
| n-Pentadecanoic acid (Pentadecylic Acid) | 0.0755 | 0.0755 | 0.0755 |
| Cholesterol | 0.151 | 0.151 | 0.151 |
| Lauric Acid | 0.0453 | 0.0453 | 0.0453 |
| 1-Docosanol (Behenyl alcohol or Docosyl Alcohol) | 0.302 | 0.302 | 0.302 |
| Squalene (Shark Origin) | 5.134 | 5.134 | 5.134 |
| Capric Acid | | | |
| Azelaic Acid | | | |
| BHT | 0.00151 | 0.00151 | 0.00151 |
| Pimelic Acid (Heptanedioic acid) | | | |
| TOTAL | 100 | 100 | 100 |

One skilled in the art would readily appreciate that the methods and compositions described herein are representative of exemplary embodiments, and not intended as limitations on the scope of the invention. It will be readily apparent to one skilled in the art that varying substitutions and modifications may be made to the present disclosure disclosed herein without departing from the scope and spirit of the invention.

All patents and publications mentioned in the specification are indicative of the levels of those skilled in the art to which the present disclosure pertains. All patents and publications are herein incorporated by reference to the same extent as if each individual publication was specifically and individually indicated as incorporated by reference.

The present disclosure illustratively described herein suitably may be practiced in the absence of any element or elements, limitation or limitations that are not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A pheromone composition for modifying behavior of an animal, the composition comprising at least 30% by weight of squalene, at least 10% by weight of linoleic acid, and at least 1% by weight of 1-docosanol, wherein the pheromone composition does not contain either palmitic acid or oleic acid.

2. A pheromone composition for modifying behavior of an animal comprising 30%-80% by weight of squalene, 10-75% by weight of linoleic acid, and 1%-10% by weight of 1-docosanol, wherein the pheromone composition does not contain either palmitic acid or oleic acid and wherein the total weight percent of all components present in the composition does not exceed 100%.

3. The pheromone composition of claim 2 comprising 30%-35% by weight of squalene, 55-65% by weight of linoleic acid, and 2%-5% by weight of 1-docosanol.

4. The pheromone composition of claim 2 comprising 65%-70% by weight of squalene, 18%-21% by weight of linoleic acid, and 2%-5% by weight of 1-docosanol.

5. The pheromone composition of claim 2, wherein the composition is dissolved in a solvent to form a pheromone solution.

6. A pheromone solution for modifying behavior of an animal comprising:
   a. between about 1% to about 30% by volume of a pheromone composition comprising 30%-35% by weight of squalene, 55-65% by weight of linoleic acid, and 2%-5% by weight of 1-docosanol, wherein the pheromone composition does not contain either palmitic acid or oleic acid; and
   b. an organic solvent; wherein the total volume percent of pheromone composition and solvent present in the pheromone solution does not exceed 100%.

7. The pheromone solution of claim 6, wherein the solvent is selected from the group consisting of ethanol, butanol, propanol, phenyl ethyl alcohol, ethylene glycol, propylene glycol, dipropylene glycol methyl ether, dipropylene glycol monoethyl ether, ether, isopropyl palmitate, chloroform, benzene, carbon disulfide, silicone fluid, oils including non-volatile and volatile oils, and combinations thereof.

8. The pheromone solution of claim 6 wherein the composition contributes between about 0.5%-15% by volume to the pheromone solution.

* * * * *